United States Patent [19]

Yoo et al.

[11] 3,954,668
[45] May 4, 1976

[54] NICKEL CONTAINING OLEFIN OLIGOMERIZATION CATALYST

[75] Inventors: Jin Sun Yoo, South Holland; Ronald L. Milam, Hazel Crest, both of Ill.

[73] Assignee: Atlantic Richfield Company, Philadelphia, Pa.

[22] Filed: Oct. 7, 1974

[21] Appl. No.: 512,785

Related U.S. Application Data

[60] Continuation of Ser. No. 257,970, May 30, 1972, abandoned, which is a division of Ser. No. 852,911, Aug. 25, 1969, Pat. No. 3,697,617.

[52] U.S. Cl.............................. 252/431 P; 252/429 B; 252/431 C
[51] Int. Cl.²........................................... B01J 31/12
[58] Field of Search........................ 260/683.15 D; 252/429 B, 430, 431 C, 431 P

[56] References Cited
UNITED STATES PATENTS

| | | | |
|---|---|---|---|
| 3,414,555 | 12/1968 | Jenkins | 260/94.3 |
| 3,483,269 | 12/1969 | Magoon et al. | 260/683.15 D |
| 3,511,891 | 5/1970 | Taylor et al. | 260/683.15 D |
| 3,592,869 | 7/1971 | Cannell | 260/683.15 D |

*Primary Examiner*—Helen M. McCarthy
*Attorney, Agent, or Firm*—Thomas J. Clough

[57] ABSTRACT

A catalyst composition for the polymerization, including oligomerization and dimerization, of olefins is provided by combining (A) a nickel source, (B) a chloro-containing electron donor ligand, and (C) a Lewis acid reducing agent, in molar ratios of (B) to (A) of about 0.5 to 15:1 and (C) to (A) of about 3 to 40:1. Preferred catalyst components are nickel acetylacetonate, chlorodiphenylphosphine and ethylaluminum sesquichloride. These catalyst compositions can be supported on a suitable carrier.

15 Claims, No Drawings

NICKEL CONTAINING OLEFIN OLIGOMERIZATION CATALYST

This is a continuation of application Ser. No. 257,970, filed May 30, 1972, now abandoned, which is a division of application Ser. No. 852,911, filed Aug. 25, 1969, now U.S. Pat. No. 3,697,617.

This invention relates to a catalyst composition and its use in the polymerization, including dimerization and oligomerization, of olefins. In particular aspects, the invention relates to a process for the formation of hexenes by dimerization of propylene and to a catalyst therefor. Such catalyst compositions can be supported on a suitable carrier.

Numerous catalysts have been disclosed in the prior art as suitable for the preparation of polymeric products of olefins, particularly to form low molecular weight dimers, trimers, tetramers, etc. of such olefins. Normally gaseous olefins such as propylene have, for example, been effectively dimerized using these catalyst systems to produce hexene fractions of varying compositions. The polymeric and oligomeric products produced in such reactions are often valuable in either the petrochemical field or the fuel industry of both. One of the major fractions of dimeric propylenes, 2-methylpentenes, can be utilized, for instance, for the synthesis of iosprene. Another propylene dimerization product, 2,3-dimethylbutene, is useful as a feed for the production of 2,3-dimethylbutadiene which in turn can be used in a multi-step synthesis of pyromellitic anhydride, or can be hydrogenated to yield 2,3-dimethylbutane, useful as an octane-enhancing ingredient in gasoline. The latter compound, for example, has the highest research octane number (103.5) of those paraffins having boiling points up to 140°F.

It has now been found that complexes of nickel with a chloro-containing electron donor ligand comprising a chlorophenylphosphine, when combined with a non-protonic Lewis acid capable of forming a coordination bond with nickel, and a reducing agent capable of reducing nickel acetylacetonate to an oxidation state of less than 2, provide a catalyst composition having highly desirable physical and chemical characteristics, and particularly, excellent catalytic activity and selectivity for the polymerization, including dimerization and oligomerization, of low molecular weight olefins. To obtain such compositions, the catalyst-forming reactants can be combined in a molar ratio of electron donor ligand to nickel of about 0.5 to 15:1, preferably about 1 to 3 to 10:1 or even about 3 to 5:1, and a Lewis acid-reducing agent to nickel molar ratio of about 3 to 40:1, preferably about 5 to 12:1.

In the preparation of the catalyst composition of the present invention, the nickel source is provided by compounds of the metal which are at least slightly soluble in some solvent wherein the nickel-phosphine ligand complex can be formed. Preferred are the weak field ligand complexes, the ligands of which readily serve in solution as transfer agents. Suitable sources of the nickel can include, for example, halides, e.g. $NiCl_2$, $NiBr_2$, $NiI_2$; dialkoxy nickel, i.e. $Ni(OR)_2$, where R represents alkyl, aryl, aralkyl, and the like groups; dialkoxy nickel carboxylate, i.e. $(RO)_2NiOOCR'$ where R and R' are as defined above as R; diphosphine complexes, e.g. $Ni[(C_6H_5)_2PC_2H_4P(C_6H_5)_2]X_2$, where X is a halide. Also available as nickel sources are chelates formed by the nickel and weak field ligands, such as $\beta$-diketones or $\beta$-keto-carboxylic acid esters and salts of carboxylic acids. Examples of these types of nickel sources include $\beta$-diketonato nickel (II), acetylacetonato nickel (II), propylacetonato nickel (II), benzoylacetonato nickel; chelates from $\beta$-ketocarboxylic acid esters; salts of saturated monocarboxylic acids, e.g. nickel formate, nickel propionate, nickel acids, e.g. nickel octoate, nickel palmitate, nickel stearate, and the like; salts of corresponding unsaturated monocarboxylic acids, e.g. nickel acrylate, nickel vinyl acetate, and the like; salts of saturated dicarboxylic acids, e.g. nickel adipate, nickel decane-1,10-dicarboxylate, and the like; salts of corresponding unsaturated dicarboxylic acids, e.g. nickel muconate and the like; salts of cyclic and aromatic carboxylic acids, e.g., nickel cyclohexane carboxylate, nickel benzoate, nickel phthalates, nickel phenylacetate and the like; and dialkoxycarboxylates, e.g. nickel dimethoxyacetate and the like. Preferred as a source of nickel is nickel acetylacetonate.

The electron donor ligand component employed in preparing the nickel complex component of the catalyst of the present invention is preferably a phosphine compound having the general formula:

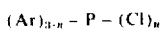

$$(Ar)_{3-n} - P - (Cl)_n$$

wherein Ar is a monovalent aryl or alkaryl radical of 6 to about 12 carbon atoms, preferably of 6 to about 9 carbon atoms and n equals 1 or 2. When Ar is an alkaryl radical, the aryl group of the radical is between the alkyl group of the radical and the phosphorus atom, i.e. phosphorus is attached to an aromatic ring carbon atom. Preferably, Ar is monocyclic. Examples of suitable phosphine compounds for the catalyst compositions of the present invention are phenyldichlorophosphine and chlorodiphenylphosphine. Such compounds have been found to be more effective in the catalyst compositions of this invention for the dimerization of olefins than phosphine compounds containing only aryl or chloride groups such as triphenylphosphine or phosphorus trichloride.

The Lewis acid and the reducing agent functions of our catalyst are preferably supplied in a single compound. As examples of such compounds, there may be mentioned the acidic metal halides which correspond to the general formula:

$$R'_{n-y}MX_y$$

wherein M is a metallic element of coordination number n whose halides are Lewis acids, X is a halogen having an atomic number of 9 to 53, i.e. fluorine, chlorine, bromine, iodine, R' is hydrocarbyl, e.g. alkyl, of 2 to about 6 carbon atoms and y is a number having a value from 1 to n; preferably y is at least one less than n so that R' is at least 1. Preferred metallic elements in the above compound include aluminum, magnesium, beryllium, lead, zinc, and tin. Examples of suitable such acidic metal halides include alkylaluminum halides including mono-, sesqui-, and dihalides, aluminum trichloride, zinc chloride and stannic chloride. Specific examples of suitable alkylaluminum halides are diethylaluminum chloride, fluoride, iodide, and bromide; ethylaluminum dichloride; ethylaluminum sesquichloride, etc.

Where the particular reducing agent employed in the composition does not also perform as a Lewis acid, it is necessary to separately supply the Lewis acid to the catalyst composition. Examples of reducing agents which are suitable in the preparation of the catalyst composition but which do not perform as Lewis acids therein include trialkylaluminum, monoalkoxydialkylaluminum and dialkylaluminum hydrides wherein the alkyl and alkoxy groups contain up to about 6 carbon atoms. Other examples are Grignard reagents, allyl and alkyl tin complexes, and the like. The reducing agent must be compatible with the Lewis acid and be capable of reducing nickel acetylacetonate, preferably to an oxidation state lower than 2 and even to 0.

Where the reducing agent does not also function as a Lewis acid, an additional Lewis acid component can be supplied by a compound which is other than a protonic or hydrogen acid and which is capable of receiving one or more pairs of electrons to form a coordination bond. Lewis acids are well known to the art and are fully defined for example by Noller, *Chemistry of Organic Compounds*, W. B. Saunders, 1951, at pages 233–235, by Stone, *Chemical Review* (1958) at page 101, and by G. N. Lewis, *Journal of the Franklin Institute* (1938), pages 226–293. Examples of Lewis acids which are not included as a component of a compound which also serves as a reducing agent include boron-trifluoride, boron-trifluoride etherates, e.g. diethyletherate, aluminum trihalides, zinc halides and stannic halides.

The relative proportions of the components of the catalyst composition, i.e., the nickel, the Lewis acid and reducing agent, and the electron donor ligand, determine the catalytic character of the composition. The catalyst composition is ordinarily formed by using an electron donor ligand-to-nickel mole ratio of about 0.5 to 15:1, preferably about 1 or 3 to 10:1 or even about 3 to 5:1. The amount of the Lewis acid-reducing agent, e.g. ethyl aluminum sesquichloride, can preferably vary in more or less direct proportion with the ratio of electron donor ligand-to-nickel, generally increasing as the ligand is increased.

A solid support suitable for use in the catalyst of the present invention is an acidic, silica-based material e.g. having a D + L activity of at least about 20, preferably at least about 30 when determined according to the method of Birkhimer et al., "A Bench Scale Test Method for Evaluating Cracking Catalysts," Proceedings of the American Petroleum Institute, Division of Refining, Vol. 27(III), page 90 (1947) and hereinafter referred to as Cat A. The silica-based support preferably has a substantial surface area as determined by the BET nitrogen absorption procedure (JACS, Vol. 60, pp. 309 et seq. (1938). The surface area of the support can be at least about 50 square meters per gram, and such surface areas are often up to about 500 or more $m^2/gm$, preferably about 150 to 400 $m^2/gm$. It is preferred that the catalyst support be relatively dry to avoid undue reaction with and loss of catalytic promoting materials. Thus it is advantageous that the support be calcined, e.g. at temperatures of about 600° to 1500°F. or more, to reduce the water content, but such calcination should not be so severe that the support is no longer catalytically-active.

The support component can contain other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of or even to a major extent of silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings with diameters in the 6 to 15 Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500°F., to convert the silica-alumina hydrogel to xerogel form. The dried material can then be calcined, e.g., at a temperature of about 700° to 1500°F., preferably about 800° to 1400°F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 to ½ inch or more in diameter and about 1/32 to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by co-precipitation or sequential precipitation by either component being the initial material with at least the principal part of the silica or alumina being made in the presence of the other. Generally the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, we may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water washed to acceptable concentrations of, for instance, sodium, and redried in the preferred procedure. The drying, especially the initial drying, is advantageously effected by spray drying to give microspheres.

The crystalline aluminosilicate which can be present in catalyst support of the present invention, can have pore openings of 6 to 15 A, in diameter and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-$a$ and rare earth metals such as cerium, etc. The metals may be present along with the ammonium or hydrogen cations.

The order in which components are combined to prepare the supported catalyst of the present invention can be varied. The catalysts can be conveniently prepared by impregnating the silica-based support material with a solution of the nickel component, e.g., nickel acetylacetonate, in a solvent, e.g., methanol. The nickel-impregnated support after solvent removal is then preferably sequentially contacted with a solution of the electron donor ligand component, e.g., phenyldichlorophosphine, and then the reducing agent and Lewis acid component or components, e.g., ethyl aluminum sesquichloride.

Although the foregoing is a preferred method for preparing the catalyst of this invention, the nickel complex can first be prepared for subsequent impregnation into the silica-based support. The preparation of the unsupported nickel complex can be conducted by first forming the complex of the electron donor ligand and the nickel source and then adding to a solution or suspension, of that complex, in a suitable organic solvent, the reducing agent and the Lewis acid. Suitable organic solvents are those which are inert to the catalyst and which will not enter into, or deleteriously affect, the eventual dimerization or oligomerization reaction. As specific examples thereof may be mentioned aromatic and aliphatic hydrocarbons and their halogenated, e.g., chlorinated, derivatives. Oxygen-containing solvents are generally to be avoided for this purpose.

Formation of the ligand-nickel complex may be effected by simply mixing the two reactants in the presence of a suitable solvent for the complexing reaction. The mixing can be done at room temperature or up to as high as about 300°F. The complex usually forms within about 20 to 40 minutes. Suitable solvents for the complex-forming reaction include the same solvents which are suitable for use in the final catalyst composition. If desired, however, the complexing may be accomplished in a solvent which is unsuitable for use in the final composition; in this case the resultant complex can be first isolated from the reaction mixture and re-dissolved, or re-suspended, in a proper solvent which is inert to the final catalyst composition.

Thus, for example, one method of preparing a phosphine-nickel complex can involve stirring, preferably at room temperature, a mixture of phenyldichlorophosphine, nickel acetylacetonate and toluene. After the resulting complex has been formed there may then be added directly to the reaction mixture the reducing agent and Lewis acid. In another method the complex may be prepared by refluxing an alcohol, e.g., ethanol, solution of the phosphine, say phenyldichlorophosphine, and nickel acetylacetonate, preferably at a temperature of about 150° to 250°F., and isolating the resultant complex from the reactant mixture. This approach is often preferred where the nickel reagent contains some water of hydration, as the water will be removed from the complex when the latter is separated from the alcohol solvent. The isolated complex can then be dissolved or suspended in a suitable inert solvent, e.g., toluene, and the reducing agent and Lewis acid added thereto to form the catalyst composition of the present invention. The addition to the complex solution of the reducing agent and Lewis acid is preferably conducted in a dry-inert atmosphere, out of the presence of air, for instance, in an autoclave. Within a relatively short period of time after the admixing of the components, e.g., about 5 to 15 minutes, the catalyst composition is formed, preferably as a colloidal precipitate suitable for impregnating the silica-based supports of this invention.

The catalyst compositions of this invention may be used to catalyze the production of liquid polymers, including dimers and oligomers, of ethylenically-unsaturated olefinic hydrocarbons of 2 to about 6, or even up to about 8, carbon atoms, as well as monophenyl or diphenyl derivatives thereof. By the terms "polymerization" and "polymer" it is meant to include herein copolymerization and copolymers as well as homopolymerization and homopolymers, and oligomerization and oligomers, e.g. dimerization and dimers, trimerization and trimers, etc., as well as cross- or co-oligomerization, e.g., cross- or co-dimerization, etc. For example, by cross-dimerization, used here as being synonymous with co-dimerization, is meant the addition reaction combining one mole of a first olefin, for instance propylene, with one mole of a second olefin, for instance, butene, to form one mole of a cross-dimer, for instance heptene. By dimerization, on the other hand, is meant the addition reaction which simply combines two moles of a single olefin, for instance propylene, to form the respective dimer, for instance hexene. Polymerization and polymers are the terms here used to embrace all of these reactions and reaction products.

Thus, suitable feeds include, for instance, monoethylenically unsaturated olefins, such as internal- and alpha-olefins, such as ethylene, propylene and butenes; poly-ethylenically unsaturated olefins, preferably the dienes, such as butadiene-1,3, 1-alkyl-, 2-alkyl-, 2,3-dialkyl-1,3-butadienes; and phenyl-substituted derivatives of the foregoing olefins, such as styrene, 1,4-diphenylbutadiene-1,3 and 1-phenylbutadiene-1,3. The polymers produced by the action of this present catalyst composition will often be of 2 to about 4 monomer units per molecule, i.e. will often range from dimers to tetramers. The catalyst composition has been found, for example, to be especially suitable for the production of hexene fractions by the dimerization of propylene.

Polymerization can be effected by contacting the olefinically-unsaturated feed at a temperature of, for instance, about −40°C. to 200°F., preferably about 90° to 150°F., which ordinarily can be maintained by the heat of reaction without external heating means. In many cases, it is necessary to control the temperature by cooling, as for example, by circulating a cooling medium through heat exchange tubes in the reactor. A pressure of about 10 to 600 psig, preferably about 50 to 300 psig, is suitable with the catalyst composition of the present invention. Generally, higher pressures and temperatures tend to produce higher oligomers. The amount of catalyst composition used in the reaction is that sufficient to effect polymerization of the feed, and often is about 0.05 to 5 weight percent, preferably about 0.1 to 5%, of catalyst composition (not including the solvent therefor) based on the weight of olefinic hydrocarbon feed. It has been found that when the catalyst is prepared on a high surface area support, such as, for example, a mixture of silica-alumina and alumina, advantages such as ease of handling accrue. The supported catalyst system of this invention can also be utilized in a continuous reactor for the continuous polymerization of olefins.

The preparation of an acidic silica-alumina support of this invention is illustrated by Examples I–III, and the support contains a separate phase of alumina.

EXAMPLE I

An alumina hydrogel is prepared as follows:

In a tank containing 5700 gallons of water at 85°F., are dissolved 300 lbs. of soda ash. When the soda ash has been dissolved, 180 gallons of a 39% concentration aqueous sodium aluminate solution are pumped into the tank in about a 15-period. The contents of the tank are at about 84°F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallons per minute over a 7½ minute addition period. The contents of the tank are heated to about 100°F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90°F., and 865 gallons of sodium silicate solution (28.8 weight percent $SiO_2$, 40–41.5 Baume at 68°F. and $Na_2O:SiO_2$ ratio of 1:3.2) is added. The batch is stirred for five minutes. The concentration of the sodium silicate, as $SiO_2$, in the batch is 6.3 weight percent.

With the batch at 90°F., 302 gallons of 34.5 weight percent sulfuric acid solution at 182°F. are added over a period of 45 minutes. The gel forms about 35 minutes after acid addition is begun. Then the pH is adjusted to 8.0–8.5. The batch is agitated for ten minutes.

Then 715 gallons of alum (7.8 weight percent, as $Al_2O_3$) is added to the gel over a period of about 36 minutes. The batch is agitated for an additional five minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for one hour. The finished batch has a pH of 5.5 to 5.6 and a temperature of about 110°F. The aqueous gel mixture is then pumped to a dewatering filter, and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propeller, for about 10 minutes to give a thorough dispersion. The product was stirred one minute at 14,500 rpm., in a Waring Blender and dried in a laboratory spray-drier. The spray-dried material was washed with water to acceptable impurity levels and dried at 230°F. The washed and dried material analyzed 0.08% $SO_4$ and less than 25 ppm $Na_2O$. The dried material as such was used as the catalyst support, as were extruded forms thereof and tablets (pellets) having diameters of about ⅛ inch and lengths of about ⅛ to ½ inch. Before use the catalyst support was calcined in a muffle furnace by raising the temperature by 300°F. per hour until 1350° F. was reached. This temperature was then held for three hours. The calcined particles had a surface area of about 320 to 340 square meters per gram.

The preparation and utilization of the catalyst of the present invention are illustrated by the following examples. Details of reaction conditions, catalyst compositions, and product distribution for these examples are listed in Tables I through IV. Excessive amounts of chlorodiphenylphosphine, phenyldichlorophosphine and the aluminum compound were employed in these examples and the amounts of these components may be reduced considerably.

EXAMPLE IV

A catalyst prepared from 1.03 m. moles (millimoles) nickel acetylacetonate, Ni(acac)$_2$, 3.09 m. moles chlorodiphenylphosphine, $\phi_2$PCl, and 9.80 m. moles diethylaluminum chloride, $Et_2AlCl$, in toluene was supported on 10.0 grams of a silica-alumina support having a separate alumina phase and prepared according to Example III in pellet form. Propylene in the amount of 1.85 moles was introduced to the resulting supported catalyst in a 300 cc stainless steel bomb. The system was immersed in a constant temperature bath maintained at 147°F. Periodical agitation of the reactor was applied from time to time and propylene was allowed to react at system pressures of 380 to 90 psig for a period of 3 hours. The pressure drop observed during this period was 290 psig. A clear reaction mixture was removed from the reactor and the products were analyzed by gas chromatographic techniques. The propylene feed was converted in a yield of about 82 percent to about 10 percent 2,3-dimethylbutenes, 48 percent 2-methylpentenes, 2 percent n-hexenes and 41 percent high oligomers. The results of this reaction are listed in Tables I and II.

EXAMPLE V

A mixture of tri-isobutylaluminum, $(Bu^i)_3Al$, and anhydrous aluminum chloride, $AlCl_3$, was prepared by weighing 9.80 m. moles $AlCl_3$ into a 25 percent toluene solution of 9.80 m. moles $(Bu^i)_3Al$. The mixture was maintained under a nitrogen atmosphere at room temperature overnight and the supernatant liquid was separated by means of a syringe needle from the settled solid phase. The catalyst was prepared by injecting the separated supernatant liquid into a system containing 1.04 m. moles Ni(acac)$_2$, 3.18 m. moles $\phi_2$PCl and 10.0 grams of the pelletized support employed in Example IV. With the resulting supported catalyst in a 300 cc stainless steel bomb, propylene was reacted at 147°F. for a 3 hour period to provide an 81 percent yield of a product containing about 3.5 percent 2,3-dimethylbutenes, 33 percent 2-methylpentenes, 15 percent n-hexenes and 47 percent heavy product.

EXAMPLE VI

Anhydrous $AlCl_3$ in the amount of 10.3 m. moles was added to a 29 percent solution of 10.3 m. moles tri-n-propylaluminum $(Pr^n)_3$ Al, in chlorobenzene, and maintained overnight under a nitrogen atmosphere at room temperature. The supernatant liquid, which was isolated from the settled solid phase, was injected into a system containing 1.03 m. moles Ni (acac)$_2$, 3.50 m. moles $\phi_2$PCl and 10.0 grams of the pelletized support employed in Example IV. Propylene was allowed to react with the resulting supported catalyst under conditions similar to those of Example V. A slightly higher conversion of propylene (about 83 percent) was obtained, and the product was composed of about 6 percent 2,3-dimethylbutenes, 31 percent 2-methylpentenes, 12 percent n-hexenes and 50 percent heavy oligomers. Tables I and II list details of the results.

EXAMPLE VII

The catalyst, which was prepared from 1.00 m. moles Ni (acac)$_2$, 3.09 m. moles $\phi_2$PCl and 10.2 m. moles $(Bu^i)_3Al$ was supported on 10.0 grams of the pelletized support employed in Example IV. Propylene was allowed to react with the resulting supported catalyst under conditions similar to the previous examples but only 23 percent of the propylene feed was converted to the products. Tri-isobutylaluminum was considerably less effective for generation of an active catalyst species.

EXAMPLE VIII

The catalyst was prepared from 1.00 m. moles Ni(acac)$_2$, 3.32 m. moles $\phi_2$PCl and 9.4 m. moles ethylaluminum sesquichloride, $Et_3Al_2Cl_3$, on 10.0 grams of the pelletized support employed in Example IV. Two consecutive runs were made with the resulting supported catalyst. In the first run propylene (1.85 moles) was fed to the catalyst in a 300 cc. stainless steel bomb, which was immersed in a 144°F. bath. The reactor was agitated periodically and the system was maintained under a pressure of about 120 psig for about a three hour period. Conversion of propylene was about 83 percent. In a second run, the five hour-aged catalyst was used and propylene was fed into the bomb containing the aged catalyst, whereupon the system was retained at room temperature for 24 hours with little agitation. About 74 percent of the propylene was reacted and the product contained about 6 percent 2,3-dimethylbutenes, 33 percent 2-methylpentenes, 13 percent n-hexenes and 48 percent high oligomers. Tables I and II list the results obtained in these runs.

EXAMPLE IX

The catalyst was prepared from 1.00 m. moles Ni(acac)$_2$, 6.05 m. moles phenyldichlorophosphine, $\phi$PCl$_2$, and 9.4 m. moles Et$_3$Al$_2$Cl$_3$ with 10.0 grams of the pelletized support employed in Example IV. The resulting supported catalyst was used for the oligomerization of 150 ml. propylene under conditions similar to those of previous examples. Higher propylene conversion (86 percent) was observed and the product was composed of about 7 percent 2,3-dimethylbutenes, 33 percent 2-methylpentenes, 13 percent n-hexenes and 47 percent high oligomers. The results, which are listed in Tables I and II, indicate that $\phi$ PCl$_2$ provides a slightly more active catalyst than the $\phi_2$PCl ligand.

EXAMPLE X

The catalyst was prepared from 1.03 m. moles Ni(acac)$_2$, 6.90 m. moles PCl$_3$ and 10.0 m. moles Et$_3$Al$_2$Cl$_3$ supported on 10.0 grams of the pelletized support employed in Example IV. Propylene was allowed to react on the resulting supported catalyst at 148°F. for about three hours. The pressure drop observed was 195 psig, which was less than that observed (about 290 psig) in the catalytic system with $\phi_2$PCl or $\phi$PCl$_2$. A considerably lower conversion of propylene (about 67 percent) and an unusually high portion of heavy product (about 74 percent) were obtained. The results in Tables I and II clearly demonstrate that the PCl$_3$ ligand is a less effective electron donor ligand than either the $\phi_2$PCl or $\phi$PCl$_2$ ligand.

EXAMPLE XI

A supported catalyst was prepared from 1.01 m. moles Ni(acac)$_2$, 3.02 m. moles triphenylphosphine, $\phi_3$P, and 9.6 m. moles Et$_3$Al$_2$Cl$_3$ with 10.0 grams of the pelletized support employed in Example IV and the reaction with propylene was allowed to proceed under conditions similar to that indicated in previous examples. The product (about 78 percent yield) contained 7 percent 2,3-dimethylbutenes, about 43 percent 2-methylpentenes, about 15 percent n-hexenes and about 36 percent high oligomers. A remarkable decrease of the higher oligomer product was observed with the $\phi_3$P ligand.

EXAMPLE XII

A supported catalyst was prepared from 5.0 m. moles Ni(acac)$_2$, 26.2 m. moles $\phi_2$PCl and 47.5 m. moles Et$_3$Al$_2$Cl$_3$ with 50.0 grams of the pelletized support employed in Example IV. The catalyst was transferred to a continuous tubular reactor and propylene was pumped to the reactor at the rate of 8.1 + 0.1 weight hourly space velocity. The reaction mixture was released to 500 psig through a Grove Valve for a three hour period. Four consecutive samples were collected and analyzed by gas chromatographic techniques. As shown in Table III the conversion of the propylene feed was substantially decreased from the first to the fourth sample (from 79 to 41 percent). Also the percentage of high oligomer products increased from 17 to 25 percent. The composition of the product is shown in Table III.

EXAMPLE XIII

A study was made of the use of a calcined commercial alumina support material with the compositions of this invention. To 10.0 grams of the alumina support impregnated with 0.95 m. moles Ni(acac)$_2$ was added 3.94 m. moles $\phi_2$PCl to obtain a light orange-green colored solution. After the system was allowed to react for two hours, a 25 percent toluene solution of Et$_3$Al$_2$Cl$_3$ (10.1 m. moles) was added to yield a dark brown suspension with dark brown precipitate. Upon standing for about one hour, the dark brown liquid was removed along with some of the dark brown precipitate. The separated yellowish brown pellets were transferred to a 300 cc. stainless steel bomb. Propylene (C.P. grade, 1.85 moles) was then added to the bomb and the system was submerged in a constant temperature bath set at 150°F. The propylene was allowed to react with occasional agitation for a three hour period. As soon as the reaction was discontinued, the bomb was chilled at −78°C. and a 10 ml. portion of the reaction mixture was taken for gas chromatographic analysis. The results as listed in Table IV indicate that the alumina support was a less effective base material than the silica-alumina support employed in the previous examples for the Ni(acac)$_2$—$\phi_2$PCl—Et$_3$Al$_2$Cl$_3$ system.

EXAMPLE XIV

A study was made using a second base alumina material similar to the alumina employed in the catalyst of Example IV, using the same reaction as Example XIII. As shown in Table IV this alumina base provided a supported catalyst system which produced a lower yield than either the system of Example IV or Example XIII.

Table I

| Example | Catalyst Component | | | Reaction Conditions | | | | |
|---|---|---|---|---|---|---|---|---|
| | Ni(acac)$_2$ m.mole | Electron Donor Ligand m.mole | Aluminum Compound m.mole | Pelletized Support grams | Hours Aged | Press. Drop psig. | Temp. °F. | Reaction Period, min. |
| IV | 1.03 | $\phi_2$ClP 3.09 | Et$_2$AlCl 9.80 | 10.0 | — | 290 | 147 | 180 |
| V | 1.04 | 3.18 | (Bu$^i$)$_3$Al+AlCl$_3$ 10.3 | 10.0 | — | 245 | 147 | 190 |
| VI | 1.03 | 3.50 | (Pr$^n$)$_3$Al+AlCl$_3$ 9.50 | 10.0 | — | 280 | 147 | 185 |
| VII | 1.00 | 3.09 | (Bu$^i$)$_3$Al 10.2 | 10.0 | — | 25 | 147 | 185 |
| VIII(A) | 1.00 | 3.32 | Et$_3$Al$_2$Cl$_3$ 9.4 | 10.0 | — | 230 | 144 | 185 |
| VIII(B) | 1.00 | 3.32 | Et$_3$Al$_2$Cl$_3$ 9.4 | 10.0 | 5 | — | 78 | 24 hrs. |
| IX | 1.00 | $\phi$Cl$_2$P 6.05 | Et$_3$Al$_2$Cl$_3$ 9.4 | 10.0 | — | 295 | 144 | 185 |

Table I-continued

| Example | Catalyst Component Ni(acac)₂ m.mole | Electron Donor Ligand m.mole | Aluminum Compound m.mole | Pelletized Support grams | Hours Aged | Reaction Conditions Press. Drop psig. | Temp. °F. | Reaction Period, min. |
|---|---|---|---|---|---|---|---|---|
| X | 1.03 | PCl₃ 6.90 | Et₃Al₂Cl₃ 10.3 | 10.0 | — | 195 | 148 | 185 |
| XI | 1.01 | φ₃P 3.02 | Et₃Al₂Cl₃ 9.6 | | | 255 | 147 | 185 |

Table II

| Example | Run No. | Feed | Product Distribution 2,3-DMC₄[1] wt. % | 2-MC₅ | n-C₆ | C₆⁺ | Unk | Total Product | Conversion % |
|---|---|---|---|---|---|---|---|---|---|
| IV | — | C₃⁼ | 9.8 | 47.8 | 1.7 | 40.8 | — | 64 | 82.1 |
| V | — | C₃⁼ | 3.5 | 33.0 | 14.7 | 47.3 | 1.4 | 63 | 80.8 |
| VI | — | C₃⁼ | 6.3 | 31.3 | 11.7 | 49.5 | 1.2 | 65 | 83.4 |
| VII | — | C₃⁼ | 3.4 | 30.8 | 14.1 | 46.8 | 4.9 | 18 | 23.0 |
| VIII | 1st | C₃⁼ | 7.6 | 35.4 | 12.6 | 44.5 | — | 65 | 83.4 |
| | 2nd | C₃⁼ | 6.4 | 33.1 | 12.8 | 47.6 | — | 58 | 74.4 |
| IX | — | C₃⁼ | 6.7 | 32.6 | 13.2 | 47.4 | — | 67 | 86.0 |
| X | — | C₃⁼ | 2.2 | 17.6 | 5.5 | 74.3 | 0.6 | 52 | 66.7 |
| XI | — | C₃⁼ | 7.0 | 42.6 | 14.9 | 35.5 | — | 61 | 78.4 |

Note:
[1] 2,3-DMC₄ = 2,3-dimethylbutene; n-C₆ = n-hexene; etc.

Table III

Continuous Reaction

| Example | Catalyst Component Ni(acac)₂ m.mole | φ₂PCl m.mole | Et₃Al₂Cl₃ m.mole | Pelletized Support grams | Hours Aged | Reaction Conditions Press. psig | Temp. °F. | Reaction Period, hr. | WHSV, propylene |
|---|---|---|---|---|---|---|---|---|---|
| XII | 5.0 | 26.2 | 47.5 | 50.0 | — | 500 | 108–140 | 3 | 8.1±0.1 |

| Example | No. of Sample | Sampling Period, hr | 2,3DCM₄ wt. % | 2MC₅ | nC₆ | C₆⁻ | Total Product wt g | Conversion % | Temp °F. |
|---|---|---|---|---|---|---|---|---|---|
| XII | 1st | 0–½ | 10.2 | 56.8 | 15.8 | 17.0 | 226 | 79.3 | 127–140 |
| | 2nd | ½–1 | 10.5 | 58.5 | 15.2 | 15.6 | 189 | 66.8 | 118–127 |
| | 3rd | 1–2 | 9.6 | 53.8 | 14.4 | 22.0 | 299 | 53.4 | 113–118 |
| | 4th | 2–3 | 9.2 | 52.2 | 14.0 | 24.5 | 231 | 41.2 | 108–113 |

Table IV

| Example | Catalyst Component Ni(acac)₂ m.mole | φ₂PCl m.mole | Et₃Al₂Cl₃ m.mole | Base Material grams | Reaction Conditions Press. psig | Temp. °F | Reaction Period hr. |
|---|---|---|---|---|---|---|---|
| XIII | 0.95 | 3.94 | 10.1 | Alumina 10.0 | ~360 | 150 | 3 |
| XIV | 1.01 | 4.84 | 10.1 | Alumina 10.0 | ~400 | 150 | 3 |

| Example | Product Distribution 2,3-DMC₄ | 2MC₅ | nC₆ | C₆⁺ | Conversion |
|---|---|---|---|---|---|
| XIII | 5.4 | 43.5 | 12.0 | 39.2 | 27.6 |
| XIV | 0.7 | 11.4 | 4.3 | 83.6 | 18.9 |

It is claimed:
1. A catalyst comprising a complex consisting essentially of
A. a nickel compound selected from the group consisting of nickel halide, a nickel hydrocarbyl ditertiary phosphine complex, dialkoxy nickel, dialkoxy nickel carboxylate, a nickel salt of a carboxylic acid, a nickel chelate of a beta-diketone, and a nickel chelate of a beta-ketocarboxylic acid ester, and
B. a chloro-containing electron donor ligand of a phosphorus compound having the general formula:

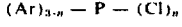

wherein Ar is a monovalent aryl radical of six to about 12 carbon atoms and $n$ equals 1 or 2, with
C. a non-protonic Lewis acid reducing agent capable of reducing nickel acetylacetonate to an oxidation state of less than 2 and capable of forming a coordination bond with nickel, represented by the formula:

wherein R is hydrocarbyl, M is a metallic element of coordination number n' whose halides are Lewis acids, X is halogen having an atomic number of 9 to 53, and Y is a number having a value of from 1 to n'−1 on a solid, acidic silica-based support, the molar ratio of B to A being about 3 to 10:1 and the molar ratio of C to A being about 3 to 40:1, said components C and A being combined to reduce nickel represented by A to an oxidation state of less than 2 and components A, B and C are present in a mole ratio which provides a colloidal precipitate fixed on the solid acidic silica-based support and which when combined produce an effective oligomerization catalyst.

2. A catalyst of claim 1 wherein X is chlorine, R is alkyl of two to about six carbon atoms, and M is selected from the group consisting of aluminum, magnesium, beryllium, lead, zinc and tin.

3. A catalyst of claim 2, wherein M is aluminum.

4. A catalyst of claim 1 wherein the electron donor ligand is selected from the group consisting of phenyldichlorophosphine and chlorodiphenylphosphine, and the molar ratio of B to A is about 3 to 10:1 and of C to A is about 5 to 12:1.

5. A catalyst of claim 2 wherein the electron donor ligand is selected from the group consisting of phenyldichlorophosphine and chlorodiphenylphosphine, and the molar ratio of B to A is about 3 to 10:1 and of C to A is about 5 to 12:1.

6. A catalyst of claim 1 wherein component A is selected from the group consisting of nickel halide, dialkoxy nickel, dialkoxy nickel carbonxylate, a nickel salt of a carboxylic acid, a nickel chelate of a beta-diketone, and a nickel chelate of a beta-ketocarboxylic acid ester.

7. A catalyst of claim 2 wherein component A is selected from the group consisting of nickel halide, dialkoxy nickel, dialkoxy nickel carboxylate, a nickel salt of a carboxylic acid, a nickel chelate of a beta-diketone, and a nickel chelate of a beta-ketocarboxylic acid ester.

8. A catalyst of claim 3 wherein component A is selected from the group consisting of nickel halide, dialkoxy nickel, dialkoxy nickel carboxylate, a nickel salt of a carboxylic acid, a nickel chelate of a beta-diketone, and a nickel chelate of a beta-ketocarboxylic acid ester.

9. A catalyst of claim 5 wherein component A is selected from the group consisting of nickel halide, dialkoxy nickel, dialkoxy nickel carboxylate, a nickel salt of a carboxylic acid, a nickel chelate of a beta-diketone, and a nickel chelate of a beta-ketocarboxylic acid ester.

10. A catalyst of claim 8 wherein component A is nickel acetylacetonate, and the support is calcined silica alumina.

11. A catalyst of claim 9 wherein component A is nickel acetylacetonate, and the support is calcined silica alumina.

12. A catalyst of claim 1 wherein the support is calcined silica alumina.

13. A catalyst of claim 3 wherein the support is comprised of about 45 to 95 weight percent amorphous silica alumina and about 5 to 55 weight percent alumina, the total alumina content of said support being about 20 to 70 weight percent.

14. A catalyst of claim 4 wherein the support is comprised of about 45 to 95 weight percent amorphous silica alumina and about 5 to 55 weight percent alumina, the total alumina content of said support being about 20 to 70 weight percent.

15. A catalyst of claim 8 wherein the support is comprised of about 45 to 95 weight percent amorphous silica alumina and about 5 to 55 weight percent alumina, the total alumina content of said support being about 20 to 70 weight percent.

* * * * *